US011480462B2

(12) United States Patent
Hazan et al.

(10) Patent No.: US 11,480,462 B2
(45) Date of Patent: Oct. 25, 2022

(54) MONITORING DEVICE FOR AGRICULTURE INCLUDING SOLAR RADIATION SENSOR AND HANGER TO HANG THE HOUSING OF THE DEVICE ON A HANGING ELEMENT

(71) Applicant: MORE GROFIT AGTECH LTD, Nes Ziona (IL)

(72) Inventors: Avraham Yohai Hazan, Shuva (IL); Itay Miyara, Nes Ziona (IL)

(73) Assignee: MORE GROFIT AGTECH LTD, Nes Ziona (IL)

( * ) Notice: Subject to any disclaimer, the term of this patent is extended or adjusted under 35 U.S.C. 154(b) by 191 days.

(21) Appl. No.: 16/771,444

(22) PCT Filed: Dec. 13, 2018

(86) PCT No.: PCT/IL2018/051356
§ 371 (c)(1),
(2) Date: Jun. 10, 2020

(87) PCT Pub. No.: WO2019/116373
PCT Pub. Date: Jun. 20, 2019

(65) Prior Publication Data
US 2021/0072072 A1    Mar. 11, 2021

Related U.S. Application Data

(60) Provisional application No. 62/598,479, filed on Dec. 14, 2017.

(51) Int. Cl.
*G01J 1/42* (2006.01)
*G01J 1/02* (2006.01)
(Continued)

(52) U.S. Cl.
CPC .............. *G01J 1/0271* (2013.01); *A01G 7/00* (2013.01); *G01J 1/42* (2013.01); *G01K 1/08* (2013.01);
(Continued)

(58) Field of Classification Search
CPC .... G01J 1/0271; G01J 1/42; G01J 2001/4266; G01J 2001/4276; G01K 1/08; G01W 1/11; G01W 1/12; G01W 2201/00
(Continued)

(56) References Cited

U.S. PATENT DOCUMENTS 3,308,299 A * 3/1967 Dardarian ............... G01S 3/787
250/233
3,509,355 A    4/1970 Wallace et al.
(Continued)

FOREIGN PATENT DOCUMENTS

CN    104199393 A    12/2014
DE    19913955 A1    11/1999
(Continued)

OTHER PUBLICATIONS

International Search Report and Written Opinion from International Application No. PCT/IL2018/051356 dated May 10, 2019.
(Continued)

*Primary Examiner* — Que Tan Le
(74) *Attorney, Agent, or Firm* — Dorsey & Whitney LLP (57) ABSTRACT

A monitoring device for agricultural use comprising a housing adapted to accommodate at least a solar radiation sensor positioned in the top portion of the housing, the housing comprising an aperture at the top end adapted to allow the solar radiation sensor to be exposed through the aperture. The housing is attached to a hanger located at the same level or below the top end of the housing and adapted to hang the housing on a hanging element such as a cable. The housing
(Continued)

may further comprises a leveling component for leveling the solar radiation sensor or the entire monitoring device. The monitoring device optionally comprises a shading sleeve compatible with passing the hanging element through the monitoring device.

22 Claims, 4 Drawing Sheets

(51) Int. Cl.
*A01G 7/00* (2006.01)
*G01K 1/08* (2021.01)
*G01N 33/24* (2006.01)
*G01W 1/02* (2006.01)

(52) U.S. Cl.
CPC .............. *G01N 33/24* (2013.01); *G01W 1/02* (2013.01); *G01J 2001/4266* (2013.01)

(58) Field of Classification Search
USPC .............................................. 250/203.4, 239
See application file for complete search history.

(56) References Cited

U.S. PATENT DOCUMENTS

| | | |
|---|---|---|
| 4,710,618 A | 12/1987 | Matsumoto et al. |
| 2002/0047085 A1 | 4/2002 | Sumiya |
| 2007/0260400 A1 | 11/2007 | Morag et al. |
| 2010/0038440 A1 | 2/2010 | Ersavas |
| 2011/0035059 A1 | 2/2011 | Ersavas |
| 2012/0055244 A1 | 3/2012 | Dolce |
| 2013/0226357 A1 | 8/2013 | Ersavas et al. |
| 2014/0288850 A1 | 9/2014 | Avigdor et al. |
| 2014/0371928 A1 | 12/2014 | Ersavas et al. |
| 2015/0081058 A1 | 3/2015 | Oliver et al. |
| 2015/0100168 A1 | 4/2015 | Oliver et al. |
| 2015/0146133 A1 | 5/2015 | Ning et al. |
| 2016/0135389 A1 | 5/2016 | Ersavas et al. |

FOREIGN PATENT DOCUMENTS

| | | |
|---|---|---|
| JP | 2015210132 A | 11/2015 |
| WO | 0138896 A1 | 5/2001 |
| WO | 2004040965 A1 | 5/2004 |
| WO | 2007143517 A2 | 12/2007 |

OTHER PUBLICATIONS

Measure the Atmosphere, Meter Environment, https://www.metergroup.com/environment/atmos/ last accessed Jun. 10, 2020.

Culler, et al., "Guest Editors' Introduction: Overview of Sensor Networks", Computer, IEEE Computer Society, vol. 37, No. 8, XP011116555, Aug. 1, 2004, pp. 41-49.

* cited by examiner

MONITORING DEVICE FOR AGRICULTURE INCLUDING SOLAR RADIATION SENSOR AND HANGER TO HANG THE HOUSING OF THE DEVICE ON A HANGING ELEMENT

TECHNICAL FIELD

The present invention relates to a monitoring device comprising at least one sensor. More particularly, the invention relates to an agricultural monitoring device comprising at least one sensor, and more specifically, for precision agriculture.

BACKGROUND ART

Precision agriculture is a powerful tool for increasing crop yield more efficiently while reducing costs, waste and redundant labor to the farmer. Sensors and cameras are deployed to collect environmental parameters in the vicinity of the crop such as temperature, moisture, radiation, soil pH and soil nutrition parameters and physical plant condition. The data is then transferred to computerized systems where it is analyzed and processed with the aid of algorithms which provide recommendations to the farmer or instructions to automated systems to which they are coupled.

Many precision agriculture systems are known. Some deploy several sensors, which are dispersed apart from each other in various locations, in order to obtain a full picture of the growing conditions. Some systems utilize radiation sensors (also known as solar radiation sensors) to obtain the amount of radiation and spectral range which the plant receives.

Evapotranspiration is one of the critical parameters which needs to be determined for irrigation regimen. It may be calculated for example by the Penman-Monteith equation which requires collection of daily mean temperature, soil heat flux density, wind speed, vapor pressure, saturation vapor pressure, air pressure, and net radiation at a height of 2 meters above crop surface. The latter is collected by a solar radiation sensor which requires to be properly installed in an open environment, without being obscured by other objects and with no tilt angle with respect to the light source, i.e. they usually need to be directed parallel to the ground (but not always).

Nowadays, in order to collect reliable net radiation, radiation sensors are usually placed on an arm extending sideways from a dedicated pole which placed in the ground for this purpose.

SUMMARY OF INVENTION

The aim of the invention is to provide a monitoring device for collecting agricultural parameters, housing a solar radiation sensor optionally alongside other sensors while providing the solar radiation sensor means for accurate and reliably gathering of net radiation in the vicinity of the crop.

Another aim of the invention is to provide a monitoring device for agricultural use which requires facilitated installation.

Another aim of the invention is to eliminate the need to place a pole in the ground for installing a solar radiation sensor for agricultural use.

Another aim of the invention is to provide a monitoring device for agricultural use which can be hanged on a rope-like hanging element generally abundant in an indoor agricultural facility or which can be easily installed outdoors.

Another aim of the invention is to provide a monitoring device which allows leveling of the solar radiation sensor.

In a first aspect the invention provides a monitoring device comprising a housing, and a solar radiation sensor and a hanger. In some embodiments the monitoring device further comprises a leveling component. The housing is adapted to accommodate at least a solar radiation sensor. The housing comprises a bottom end, a top end, a peripheral sidewall extending from the bottom end to the top end, wherein the top end of the housing comprises a top end aperture adapted to allow the solar radiation sensor to be exposed through the aperture. The solar radiation sensor is positioned at the top portion of the housing such that it is exposed through the top end aperture. The hanger comprises a top wall and being attached to the sidewall of the housing optionally with a fastener, the top end of the hanger is located below the top end of the housing and is adapted to hang the housing on a hanging element. The optional leveling component is used for leveling the solar radiation sensor. In some embodiments the monitoring device further comprises at least one of: (i) a data storage component and (ii) an operational circuit comprising at least a communication component for receiving readings from the sensors and transmitting said readings to an external system.

In another aspect the invention provides a method for installing a monitoring device for agriculture comprising:
a. obtaining a monitoring device as defined above;
b. hanging the monitoring device on a hanging element such as a wire, pipe, branch or hose above a crop;
c. leveling the solar radiation sensor; and
d. if the monitoring device further comprises at least one of a thermometer and a hygrometer, then covering the housing with a shading sleeve while inserting the hanging element through the slots of the shading sleeve;
to obtain a monitoring device comprising a leveled solar radiation sensor having a full exposure to any light source positioned above the solar radiation sensor for efficiently collecting full and accurate photonic data.

In a further aspect, the invention provides a kit comprising a monitoring device as defined above and instructions for installing the monitoring device comprising the method as defined above.

DESCRIPTION OF EMBODIMENTS

Although the invention is illustrated and described herein as embodied in example monitoring devices, the invention is not limited to the details shown because various modifications and structural changes may be made without departing from the invention and the equivalents of the claims. However, the construction and method of operation of the invention together with additional objects and advantages thereof will be best understood from the following description of specific embodiments when read in connection with the accompanying drawings.

The present invention provides a monitoring device comprising a housing, a hanger attached to the housing, a solar radiation sensor accommodated in the housing and optionally a leveling component for leveling the solar radiation sensor. In some embodiments the monitoring device further comprises an operational circuit comprising at least one of a communication component and a data storage unit.

The device is designed for collecting and transmitting agricultural parameters in the vicinity of a crop. In some embodiments the device is used in an indoor plant growing location such as a greenhouse, a cold frame, a growing room and a growing warehouse. In some embodiments the device is installed in an open field or orchard.

In some embodiments the data is collected for providing evapotranspiration parameters in the vicinity of a plant or multiple plants to a separate system comprising installed instructions for calculating at least one equation such as the Penman Monteith equation, using said parameters and providing irrigation recommendations to a grower rendering efficiently spending resources such as irrigation, lighting and fertilization and for optimizing the yield of the crop.

The Housing

The housing comprises a bottom end, a top end, a sidewall extending from the bottom end to the top end. The housing can be any case, sheath, shell or cover of any shape or size which defines a chamber large enough to accommodate the solar radiation sensor and optionally other sensors and the operational circuit. In some embodiments, the housing may be of cylindrical shape. In some embodiment the housing comprises a cavity. In some embodiments, the housing is of a cylindrical shape comprising a cavity.

The top end of the housing comprises a top end aperture, or opening, through which the solar radiation sensor is exposed. The solar radiation sensor is placed inside the housing in the upper portion of the housing, close to the aperture. The aperture has a shape and dimensions being at least of the size of the solar radiation sensor. In some embodiments, the solar radiation sensor protrudes through the top end of the housing. In some embodiments the top surface of the solar radiation sensor is aligned with the top end of the housing. Any other sensor or component that is accommodated in the housing is placed aside or below the solar radiation sensor, but not at an elevated position with respect to the solar radiation sensor. This way, no component of the monitoring device may obscure the solar radiation sensor, allowing reliable and efficient readings of the amount of light flux in the vicinity of the crop.

In some embodiments, the sidewall of the housing comprises a groove extending inwards towards the central longitudinal axis of the housing (the axis between the center of the bottom of the housing to the center of the top). The groove defines a cavity, shaped to accommodate the hanger being attached to the outer side of the sidewall and located inside the cavity. In some embodiments, the cavity extends at least to the central longitudinal axis of the housing. In some embodiments, the hanger is attached to one of the walls defining the cavity such that the hanger resides on the central longitudinal axis of the housing. In some embodiments, the hanger is attached to one of the walls defining the cavity such that the hanger resides essentially or approximately on the central longitudinal axis of the housing.

In some embodiments, the cavity is open sided from three sides allowing access to the hanger from the front side and allowing to pass a hanging element through the sides lateral to the front side. In some embodiments the cavity encloses the top, bottom and rear sides of the hanger. In some embodiments a shutter provides closure to one of the open sides of the cavity. In this embodiments the shutter can be opened in order to allow the insertion of the hanging element and may be returned to a closed position after insertion of the latter.

In some embodiments the housing further comprises an aperture for accommodating an on/off button or a reset button which turns the sensors on or off or reset them.

In some embodiments the housing comprises an output socket for connecting an external computing device for downloading data from the sensors of the monitoring device.

The Hanger

The term "hanger" is construed as any mechanical device that fixates and positions the housing to a wire or a cable or any other hanging element, by enclaving the hanging element under a closed top end or loop, in a manner that the top end of the hanger loads the weight of the monitoring device on the hanging element.

The term "hanging element" relates to rope-like elements which are substantially linear parallel to the ground and are stretched above the line of the crop. The hanging elements may be rope like elements which are typically abundant in an indoor agricultural facility (e.g. a greenhouse) such as wires, cables, pipes, plant branches, nails, rods and hoses. In some embodiments the hanging elements can be especially installed for the purpose of hanging the device, for example, when installing the device in an open field, orchard or a garden.

The hanger is attached to the sidewall of the housing optionally with a fastener. The fastener is any element which can join the hanger to the housing in a reversible manner. In some embodiments the fastener can be for example a screw, a spike and a nut and bolt. In some embodiments the fastener is a magnet which affixes the hanger in place by magnetic attraction forces to a counter magnet or an element which can be magnetized in the presence of a magnet (e.g. ferromagnetic materials), and which is embedded in the housing wall or attached to the housing wall.

The hanger has a top end which is located at the same level or below the top end of the housing. In some embodiments the top end of the hanger is located below the top end of the housing. This arrangement prevents the hanger to obscure the solar radiation sensor and enables the solar radiation sensor to have full reception of the incoming radiation flux. This also enables the solar radiation sensor to be located at the same level or above the hanging element when the monitoring device is hanged on the hanging element. In some embodiments, when the monitoring device is hanged on the hanging element, the solar radiation sensor is located above the hanging element, so that the hanging element does not obscure the solar radiation from being fully exposed to the light source.

In some embodiments the hanger is selected from at least one snap lock conduit hanger, at least one hook optionally equipped with a safety latch, and at least one screw connected to at least two strings (e.g. one screw can be connected to at least two strings which are tied or connected to the hanging element or two screws can each be connected to a string. The length of the strings can be adjusted in order to level the monitoring device. In some embodiments the hook is an L-hook.

In some embodiments the hanger is attached to the wall of the housing inside a cavity of the housing. In some embodiments the cavity is designed to define an inner wall to which the hanger is attached, having the contact line between the hanger and the hanging element coinciding with a vertical plane of the housing (from top to bottom) comprising the center of mass of the assembly of the housing and the components of the monitoring device which are accommodated in the housing. Consequently, when the hanger is hanged on a wire the monitoring device remains in a horizontal position, and does not tilt about the hanging element.

In some embodiments, the hanger is attached to the sidewall of a housing (not inside a cavity) and to affect no tilt about the hanging element when the monitoring device is hanged on the hanging element, the weight of the hanger is designed to create a center of mass at the contact location between the hanger and the hanging element. The person of skill in the art would know how to calculate said designed weight taking into account the leverage of the hanger on the device, which is a function of relative vertical position of the hanger on the sidewall, the weight of the housing and the components it accommodates, and the distance of the hanger from the center of mass of the device without the hanger.

In some embodiments the hanger is a linear tubular rail horizontally attached to the sidewall, comprising two opposite side ends and a horizontal opening from one side end to the other side end. The horizontal opening has a vertical height of at least the diameter of a fishing string, and openings at the two ends of the tube being complementary to the hanging element. In some embodiments the opening is adapted to universally fit to any type of abundant rope like element in an indoor agricultural facility. To this end, in some embodiments, the opening is of at least 6 mm, allowing hanging of the hanger on 6 mm OD cables. Most wires, cables, branches, strings, nails and the like, which are found in indoor agricultural facilities have outer diameters ranging between 1 mm to 8 mm. Therefore according to some embodiments the opening of the hanger is between 1 mm to 10 mm to allow some margin for wider cables or wires. In some embodiments the opening of the hanger is between 1 mm to 8 mm. In some embodiments the opening of the hanger is of at least 8 mm. Having this characteristic would fit for hanging the device in outdoor locations as well (for example—on a nail fixed perpendicularly to a rod implanted in the ground).

The tubular rail can be of any desired shape as long as it allows the encasement of the hanging element inside the tubular rail. Without being limited thereto, the tubular rail can be a cylindrical tubular rail, a rectangular tubular rail, a polygonal tubular rail or an oval tubular rail.

In some embodiments, the hanger is an integral part of the sidewall of the housing. For example the cavity of the housing can be shaped as a hanger, such that the hanging element (e.g. a wire) passes through the cavity where it securely resides due to an enclaving shape of the cavity.

In some embodiments the hanger is located proximal to the top end of the housing. In some embodiments the cavity which accommodates the hanger is proximal to the top end of the housing.

In some embodiments there is a gap between the top and bottom walls of the hanger and the top and bottom walls of the cavity, respectively, leaving room for reorienting the position of the hanger for leveling the monitoring device when the monitoring device is hanging on a hanging element.

The Solar Radiation Sensor

The solar radiation sensor in the context of this invention relates to any sensor which is designed to measure influx radiation of light. Often, the light source is solar light, however, measuring radiation from other light sources such as electric light (e.g. incandescent light, fluorescent light, CFL, CCFL, high intensity discharge lamp and LEDs) is also within the scope of the invention. Therefore, the term "solar radiation sensor should be construed as a sensor for measuring radiation from various types of light sources such as solar light and electric light.

In some embodiments the solar radiation sensor is based on a silicone PIN diode. In some embodiments the solar radiation sensor is selected from a pyranometer, a 4-component ne-radiation sensor, quantum sensors, and pyrheliometers.

In order to obtain useful reading of the net light radiation it is necessary that the solar radiation sensor is placed under the light source, leveled with respect to the ground and fully exposed to the incoming light. As mentioned earlier, the solar radiation sensor is accommodated inside the housing but is exposed through the aperture on the top end of the housing. No other sensor is placed above the solar radiation sensor, so that the detecting element of the solar radiation sensor is placed above or aside any other sensor. In some embodiments another sensor maybe located such that there is an overlap between the other sensor and the solar radiation sensor without having the other sensor placed at an elevated position with respect to the detecting element of the solar radiation sensor. Having the solar radiation sensor exposed through the housing enables full exposure of the solar radiation sensor to any source of light positioned above it in any direction. In other words, it provides a 360° exposure to light in the X-Y plane perpendicular to the longitudinal axis of the monitoring device and a 180° at any direction above said X-Y plane in any plane comprising the longitudinal Z axis of the monitoring device for efficiently collecting full and accurate photonic data. The Cartesian coordinated system of the monitoring device is defined by the longitudinal axis (the axis connecting the top end of the housing and the bottom end of the housing) as the z-axis, the x and y axes define a horizontal cut plane perpendicular to the longitudinal axis, while the x-axis is perpendicular and the y axis is parallel to the horizontal opening of the hanger or the longitudinal axis of the hanger (See FIGS. 2a-2c). It should be understood that minor distortions from the aforementioned full exposure, for example—an unrelated cable passing above the monitoring device and slightly shading it, are considered to be within the scope of the present invention.

The solar radiation sensor can be affixed to the inner side of the sidewall by any customary means.

The solar radiation sensor is in communication with an operational circuit to which the recordings of the solar radiation sensor are transferred.

In some embodiments the solar radiation sensor is covered by a cover, such as a dome-shaped transparent, or partially transparent cover, which provides protection from water, dust and debris. The cover may attenuate the light intensity which is read by the sensor, and the data is normalized accordingly by the calculating system upon receiving data.

The cover of the solar radiation sensor can be reversibly connected to the top end of the housing.

The Leveling Component

Leveling the solar radiation sensor is an essential step in the installation of a solar radiation sensor in an agricultural environment. As mentioned earlier, the housing and the hanger are designed to hang on the hanging element such that if the hanging element is perpendicular to the ground then the monitoring device hangs without significant tilting about the hanging element with respect to the ground. Nonetheless, several factors might divert the orientation of the monitoring device from being leveled with the ground and consequently diverting the solar radiation sensor from being leveled. For example, the hanging device might not be perfectly linear and may suffer from deformations. In addition, occasionally the hanging element itself may not be linear or tilt with respect to the ground at the desired location for placing the monitoring device. This limits the user to choose locations for hanging the monitoring device of the invention in locations where the monitoring device would be levelled with respect to the ground. To mitigate such situations the monitoring device may further comprises a leveling component. The leveling of the solar radiation sensor relative to the ground can be achieved with the aid of a leveling component by two ways: (i) leveling the entire device (ii) leveling the solar radiation sensor itself.

Leveling the device can be met by adjusting the orientation of the hanger. To this end, the leveling component is attached to the hanger and affects the orientation of the hanger with respect to the housing. In some embodiments, the position of the hanger is adjusted along the horizontal y-axis being perpendicular to the longitudinal z-axis of the housing and the x-axis, the latter being perpendicular to the horizontal opening of the hanger. In some embodiments, the leveling component is a screw which attaches the hanger to the sidewall of the housing. In such embodiments, the user can slightly release the screw holding the hanger using a screwdriver, then rotate the hanger until the device seems to be levelled and tighten the screw back in place to affix the hanger in the position where the device is leveled. In some embodiments the levelling component is a screw of a knob attaching the hanging device to the housing, the knob facilitates the adjusting operation by the user.

In embodiments where the hanger is a set of at least two hooks being attached to the upper wall of the cavity, and the leveling is met by adjusting the relative height of the hooks, for example by screwing or sliding the hooks vertically inside a ferrule placed inside the wall of the housing. In such an embodiment, the levelling component is the hanger itself. There are numerous of other options which a person of skill in the art may implement in order to allow the adjustment of the hanger for levelling the device on the hanging element.

Alternatively, the solar radiation sensor itself can be leveled. To this end, in some embodiments, the solar radiation sensor is attached to a stage located inside the housing. The stage, or the solar radiation sensor itself can be attached to a mechanical motor which levels the solar radiation sensor by adjusting the horizontal orientation of the solar radiation sensor. In some embodiments the leveling motor is a leveling motor such as a leveling motor fit for leveling automobile headlights.

In some embodiments the leveling component is a fastener such as a knob or a screw fixating the solar radiation sensor to the housing wall or fixating the stage carrying the solar radiation sensor manually. In these embodiments the leveling component is approachable to the user for adjusting the orientation of the solar radiation sensor until it is leveled. In some of these embodiments, a level is attached to the solar radiation sensor itself to enabling an indication whether the solar radiation sensor is leveled.

The Level

In some embodiments, the device comprises a level. The term "level" in the context of the invention relates to any available instrument known in the art for ascertaining whether a surface is horizontal relative to the ground, consisting essentially of an encased, liquid-filled tube containing an air bubble that moves to a center window when the instrument is set on an even plane. The level attached to the sidewall or embedded in the sidewall, providing the user an indication of the deviation of the device and/or the solar radiation sensor from being leveled on the z-x plane.

In some embodiments the level is placed on the housing such that the longitudinal axis of level is perpendicular to the longitudinal axis of the housing, and the center of the level resides on a z-y plane which includes the center of the hanger.

In embodiments where the solar radiation sensor or the stage carrying it are directly leveled, the level is connected thereto and the housing is designed to allow the user to observe the level, for example by having an aperture or a window through which the level can be observed.

The monitoring device is designed such that when it hangs on the hanging element, the device is leveled on the y-z plane. Nonetheless, in some embodiments the housing comprises a second level positioned on the y-z plane for assuring that the housing is leveled on the y-z plane as well.

Other Sensors

In some embodiments the housing further comprises at least one additional sensor known in the art, beside the solar radiation sensor. The at least one additional sensor collects other parameters which define the environmental-agricultural conditions of the crop, and can be any type of sensor which the can provide input which is valuable to the grower and which may affect decision making with regards to growing the crop, such as irrigation, fertilizing, applying pesticides, herbicides or fungicides and so on. These parameters include but are not limited to soil moisture, soil pH, nutrients levels including ammonium, nitrites and nitrates, relative humidity, $CO_2$ levels, surface tension, electrical conductivity, water flow rate, and rainfall quantities (water volume). The at least one additional sensor can be for example a thermometer, a hygrometer for measuring relative humidity or a wind detector. In some embodiments the housing further accommodates a thermometer and a hygrometer. In some embodiments the monitoring device further comprises a detector for determining the distance of the device from the ground, i.e. a height detector.

In some embodiments the monitoring device comprises more than one solar radiation sensor. The additional solar radiation sensor may be oriented to detect side light, or reflected light arriving from the sides or from the ground. To this end the monitoring device may comprise more apertures to accommodate the additional solar radiation sensors while providing full exposure to the scanned area.

In some embodiments the monitoring device may further include a camera. The camera may be installed inside the housing and be provided with a designated aperture or it may be attached to the exterior wall of the housing. In some embodiments the camera is attached to a lower portion of the housing below the bottom end of the shading sleeve.

Any type of thermometer which can measure the ambient air temperature may be used as the thermometer of the monitoring device. In some embodiments the thermometer is an infra-red thermometer. In some embodiments the thermometer is a liquid in glass thermometer. In some embodiments the thermometer is a thermocouple. In some embodiments the thermometer is a liquid crystal thermometer. In some embodiments the thermometer is combined to a silicon chip.

All the additional sensors/detectors that are accommodated in the housing a placed at the same level or below the solar radiation sensor.

In order to allow accurate reading by the additional sensors/detectors, the housing may comprise additional apertures for exposing said additional sensors/detectors and/or for aeration of the housing.

For example the housing may comprise an aperture in the sidewall for exposing a thermometer, a hygrometer or a thermometer-hygrometer. In some embodiments an aperture is provided approximately at the center of the housing. In some embodiments the housing comprises an aperture adapted for a passage of a connection cable between the communication circuit and at least one of a wind sensor and a soil sensor for determining soil parameters such as soil moisture, a tensiometer, a pH meter, soil nutrients detector or combination thereof. In some embodiments an additional sensor is selected from a relative humidity sensor, an air $CO_2$ sensor, pH meter, $NO_3^-$ sensor, electrical conductivity sensor, volumetric water content sensor, soil temperature, $NO_2^-$ sensor, $NH_4^+$ sensor all in soil, substrate or solution and combinations thereof.

The Sleeve

In such embodiments where the housing further accommodates a thermometer and/or a hygrometer (in some embodiments the thermometer and the hygrometer are the same sensor) it is important to allow a reliable measurement of the ambient shade temperature and relative humidity, and to protect the housing from over-heating, especially if the housing includes plastic parts. To this end, the monitoring device further comprises a shading sleeve.

The shading sleeve comprises a peripheral sidewall, a top end opening, a bottom end opening and at least one slot. The peripheral sidewall is larger in its dimensions than the housing so that when the shading sleeve is assembled over the housing it defines a gap between the inner wall of the shading sleeve and the outer wall of the housing, so that air will surround the housing. To allow air exchange between the ambient air and the air surrounding the housing, the peripheral sidewall may comprise slits. In some embodiments the slits are in the form of spaced shades adapted to shade the portion of the housing accommodating the at least one of the thermometer, while allowing the air exchange through the spaces between the shades. The shades may be described as spaced slits on at least a portion of the sidewall. Different embodiments can adopt varied widths for the slits. As the sleeve is supposed to shade the portion of the housing comprising the detectors, the width of the slits depends on the tilt angle of the shades and the width of the shades. The skilled artisan would know how to make these modifications accordingly.

In some embodiments, a plurality of diagonal channels replaces the shades and the slits, wherein the outer aperture of the channel is lower than the inner aperture so that air would exchange but direct light would not penetrate.

The shading sleeve comprises at least one slot compatible with the dimensions of the hanging element allowing the hanging element to pass though said at least one slot. The slot (not to be confused with the shading slits) is compatible with the diameter of the hanging element, i.e., the width of the slot should be equal or slightly larger than the diameter of the hanging element, allowing the hanging element to pass though said at least one slot. As the diameters of most hanging elements are less than 10 mm, then an opening of 10 mm, in some embodiment 9 mm, in some embodiments 8 mm, should be adequate for hanging the monitoring device on abundant cables in an indoor agricultural facility, or easily installed outdoors.

In some embodiments the shading sleeve has two opposite slots for this purpose.

The shading sleeve is designed to cover the sides of the housing while leaving the solar radiation sensor exposed. Therefore the shading sleeve comprises a top end opening wider than the cover of the solar radiation sensor in order to leave the solar radiation sensor exposed.

In some embodiments the shading sleeve is detachably attached to the housing when it is assembled to the housing. To this end the housing and the sleeve may comprise complementary reversibly attaching means which are commonly known in the art. In some embodiments the top end of the shading sleeve is slightly tapered and narrower than the top end of the housing, or of a collar around the cover of the solar radiation sensor such that the shading sleeve resides on the top end of the housing or the collar of the cover when the shading sleeve is assembled to the housing.

In some embodiments the shading sleeve also has a bottom end opening wider than the widest section of the portion of the housing to be shaded. This enables the assembly of the shading sleeve on the housing, when the housing is hanging on the hanging element, by passing the shading sleeve over the housing through the bottom end opening until the shading sleeve covers the housing.

In such embodiments, in order to enable the covering of the housing with the sleeve while the housing is hanged on a hanging element such as a wire, the sleeve comprises two longitudinal slots, opposite and aligned to each other, through which the wire or cable may pass. To this end, the slots have an opening on the bottom end such that the wire (or other hanging element) on which the hanger is hanged can be inserted through the two slots. The top end of the slots is designed to be aligned with the hanging point at which the hanger is located, when the sleeve is assembled with the housing, or above it. When the sleeve is assembled to the hanging housing, the top end of the slots may provide a locking mechanism of the hanging element against the hanger (e.g. the rail of the hanger). The hanging element is pressed from the bottom by the hanger and from the top by the closed end of the slots of the shading sleeve.

In some embodiments, the shading sleeve comprises two parts which are reversibly attached to each other having horizontal slots positioned parallel to the position of the hanging element when the sleeve is assembled on the housing when the housing is hanging on the hanging element. The two parts of the sleeve may be connected at one longitudinal edge through an axis which allows them two open and close reversibly, such that in the open state the housing can be inserted into the sleeve and the sleeve is then closed having the housing covered inside the shading sleeve.

In other embodiments the sleeve is made of two complementary parts, one assembled on the housing from the bottom end and the other is assembled from the upper end, the two parts connect and attach to each other. At least one of the parts has a groove on opposite sides that defines an aperture allowing the wire or cable to pass through the sleeve when the two parts of the sleeve are assembled on the housing while the housing is hanging on the cable or wire.

In some embodiments the sleeve may comprise ventilation slits proximal to the top end of the sleeve and proximal to the aperture for the cover of the solar radiation sensor. This allows release of heat and another air flow pathway for air-exchange between the ambient air and the air in the volume between the inner wall of the sleeve and the outer wall of the housing.

The unique hanging mechanism of this invention allows the farmer, grower or gardener to use existing cables, wires and hoses in the indoor facility, an open field, orchard or a garden while providing the monitoring device perfect conditions to record and transfer data, especially data related to incoming light flux for further calculation of recommended steps for optimized farming steps. Nonetheless, the rope-like hanging elements can also be especially installed for the purpose of hanging the monitoring device of the invention.

In another embodiment of this invention targeted to farmers, growers or gardeners which prefer using a pole to place the monitoring device the hanger is replaced by a tether or an arm which fixates the monitoring device to said pole. In some embodiments, the hanger of the invention is hanged on the arm which has a diameter being equivalent to the diameter of a cable. The arm passes through the slot(s) of the shading sleeve and through the hanger, just as a cable or wire would. One of the ends of the arm, may comprise an attaching means such as a clamp to connect to the pole. The clamp can be adjustable for attaching the arm to poles a varied diameters.

The hanger, the housing and the shading sleeve can all be prepared from common available materials by common techniques known in the art. For example, the hanger, the housing and the shading sleeve can be prepared by molding thermoplastic materials.

The Operational Circuit

The operational circuit functions to transfer and/or store the readings of the sensors/detectors of the monitoring device to IoT (internet of things) or to a local computerized network. To this end, the operational circuit may store the data which is received from the sensors, or it may serve as a transmitter of the data, or both. The operational circuit comprises a communication component for receiving data from the solar radiation sensor and optionally from at least one other optional sensor for transmitting said data to a remote system. The operational circuit may comprise a computing device which may include a for example, a central processing unit processor (CPU), a chip or any suitable computing or computational device, an operating system, a memory, an executable code, a storage, input devices and output devices. The computing device is capable of manipulating and/or transforming data represented as physical (e.g., electronic) quantities within the computer's registers as received from the detectors/sensors of the monitoring device and/or memories into other data similarly represented as physical quantities within the computer's registers and/or memories or other information non-transitory storage medium that may store instructions to perform operations and/or processes.

A memory usable for storing programs, control instructions and data may be or may include, for example, a random access memory (RAM), a read only memory (ROM), a dynamic RAM (DRAM), a synchronous DRAM (SD-RAM), a double data rate (DDR) memory chip, a flash memory, a volatile memory, a non-volatile memory, a cache memory, a buffer, a short term memory unit, a long term memory unit, or other suitable memory units or storage units. Such memory may be or may include a plurality of, possibly different memory units. The memory may be a computer or processor non-transitory readable medium, or a computer non-transitory storage medium, e.g., a RAM.

Executable code stored in the memory and executable on the processor may be any executable code, e.g., an application, a program, a process, task or script. The executable code may be executed by the controller, possibly under control of an operating system.

The operational circuit can be configured to receive signals from the sensors/detectors of the monitoring device and transmit said signals to a remote computational system where these signals are transformed to parameters used for calculating the overall environmental conditions and derive recommendations to the grower of the crop.

The operational circuit may be placed inside the housing or it may be kept in a separate location and be in communication with the sensors/detectors of the device through wires or wireless means (such as Bluetooth® connection).

In some embodiments the data from the sensors/detectors is stored on a data storage device in the housing and the data is downloaded from the data storage device of the operational circuit by physically or wirelessly connecting a to the data storage.

The monitoring device further comprises a power source providing voltage to the components of the monitoring device which require electrical voltage in order to operate. The power source can be a battery installed in housing, or it can be a renewable energy source such as a solar panel. Alternatively the monitoring device comprises a cable for supplying electrical voltage from an external source.

In another aspect the invention provides a kit comprising the monitoring device of the invention a described herein accompanied with installation instructions according to the method described above.

In some embodiments the kit further comprises programmable instructions being installed on a processing unit of the device for managing data collected from sensors of the device.

Specific Embodiments

For better understanding of the present invention and in order to exemplify how it may be implemented in practice, several embodiments are hereby described, which should be interpreted only as non-limiting examples, with reference to the accompanying figures. It is noted that the sizes and scale of the embodiments presented in the figures are exemplary and non-limiting.

It will be appreciated that for simplicity and clarity of illustration, where appropriate, reference numerals have been repeated among the different figures to indicate corresponding or analogous elements in different embodiments. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein.

Figure 1A:
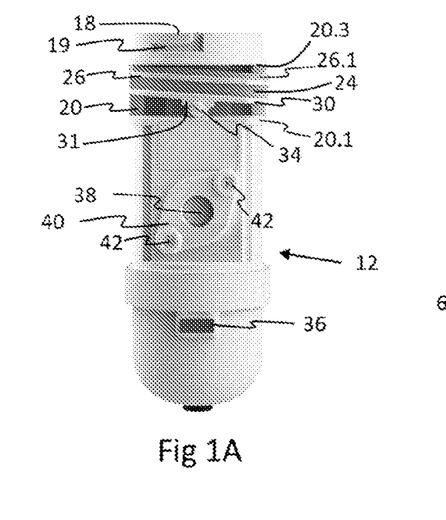
FIG. 1A depicts a front view representation of a coverless housing and hanger of a monitoring device according to an embodiment of the invention.
Figure 1B:
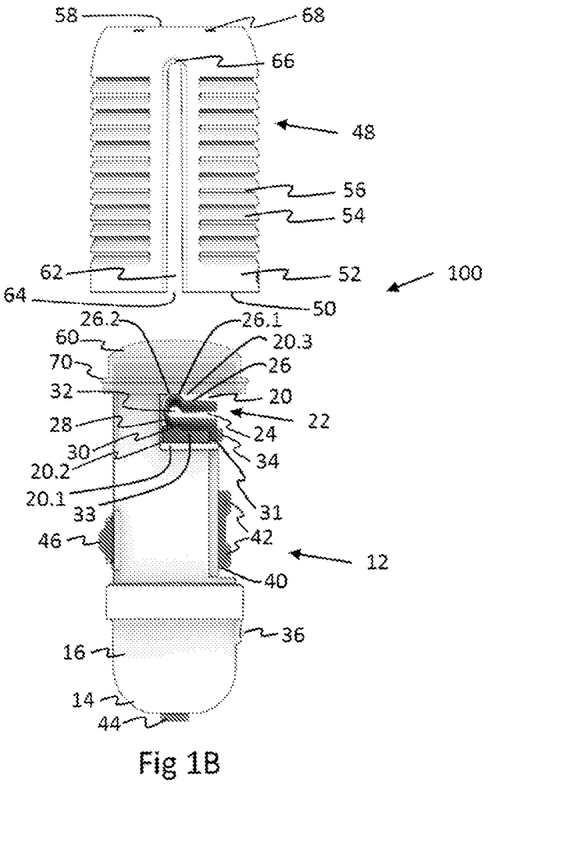
FIG. 1B. depicts a partially exploded left side view representation of a monitoring device in a disassembled form according to an embodiment of the invention.
Figure 1C:
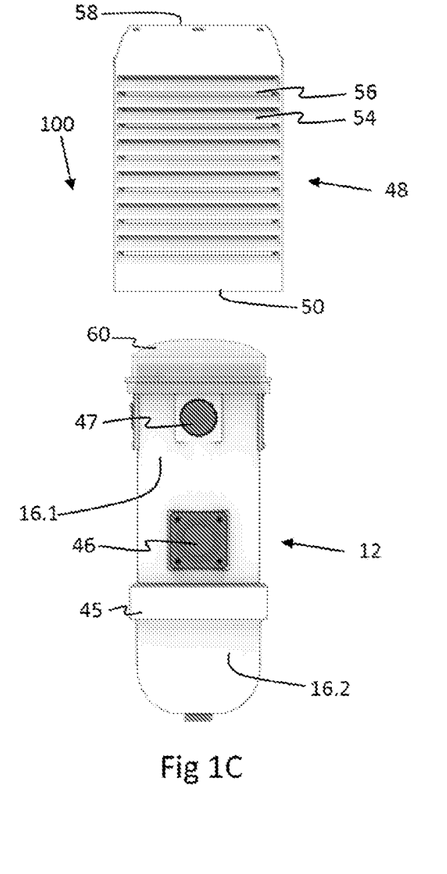
FIG. 1C depicts a partially exploded rear view representation of a monitoring device in a disassembled form according to an embodiment of the invention
Figure 2A:
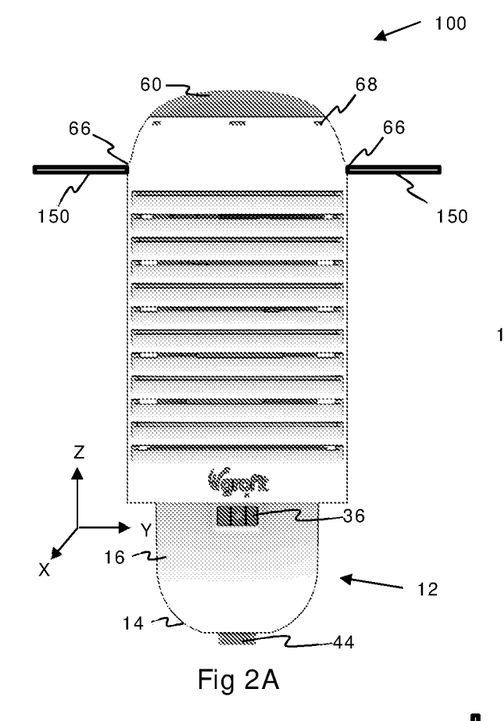
FIG. 2A depicts a front view representation of a monitoring device in an assembled form (hanging on a wire) according to an embodiment of the invention.
Figure 2B:
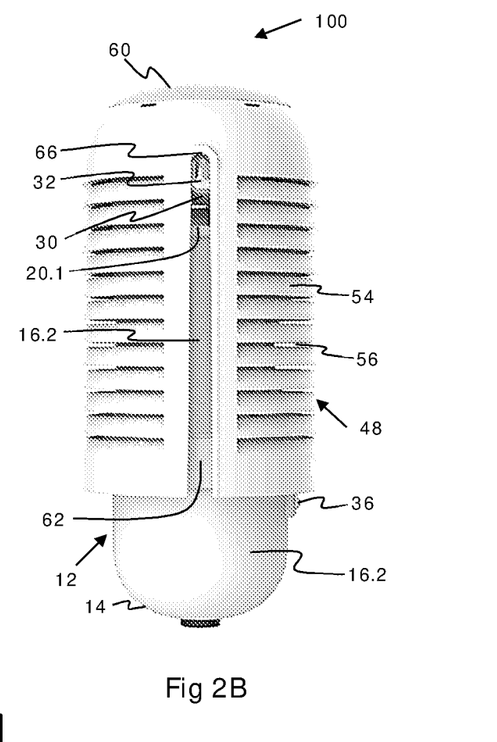
FIG. 2B depicts a left side view representation of a monitoring device in an assembled form (hanging on a wire) according to an embodiment of the invention.
Figure 2C:
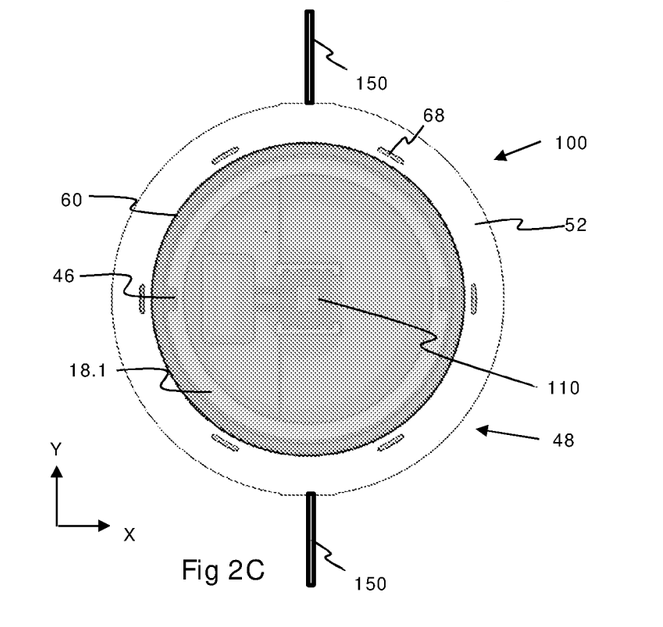
FIG. 2C depicts a top view representation of a monitoring device in an assembled form (hanging on a wire) according to an embodiment of the invention in accordance with FIG. 2A.

Reference is made to FIG. 1A, depicting the housing 12 without the cover 60 of the radiation sensor 110, to FIGS. 1B-1C depicting a partially exploded view of a monitoring device 100, wherein the shading sleeve 48 and the housing 12 are disassembled, and to FIGS. 2a to 2c depicting the monitoring device 100 in an assembled form according to an embodiment of the invention. A housing 12 accommodating a solar radiation sensor 110, a hygrometer-thermometer (a sensor measuring both temperature and humidity, positioned below the solar radiation sensor—not shown) and a controlling circuit (positioned below the solar radiation sensor—not shown) has a tapered bottom end 14, a peripheral sidewall 16 extending from the bottom end 14 to a top end 18. The top end 18 comprises an aperture (covered by cover 60, see FIG. 2C) through which the solar radiation sensor 110 is exposed. The hygrometer-thermometer is positioned inside the housing 12 below the solar radiation sensor.

The housing 12 comprises a cavity 20, where an open sided linear tubular rail hanger 22 is positioned. The cavity is defined by a bottom wall 20.1, a sidewall 20.2 and atop wall 20.3. The hanger 22 is shaped as a double open sided tubular rail. The hanger 22 comprises a horizontal opening slot 24, defined by the edges of the top wall 26 and bottom wall 30 of the hanger. The horizontal opening slot 24 is wide enough to enable most cables and wires which are abundant in a greenhouse. The top wall 26 is shaped to secure a hanging element 150 when the hanging element is inserted through the opening slot 24 inwards all the way to the back cavity 32 of the double open sided linear tubular rail hanger 22. To this end, the top wall 26 extends inward from the opening slot 24. Towards the end of the rail it concavely bends upward 26.1 and then downward 26.2, where it extends to a back wall 28 and further to the bottom wall 30. The inner cavity 32 which is defined by the curved top wall portions 26.1 and 26.2 rear wall 28 and the portion of the bottom wall 30 proximal to the rear wall 28, entraps and secures the monitoring device 100 on the hanging element 150.

The hanger 22 is attached through a tooth 31 extending from the front edge of the bottom wall 30 to a supporting lug 33 extending from the bottom wall 20.1 of the cavity 20, and rear wall 20.2 of the cavity 20 by a screw 34. The screw 34 serves as the leveling component in this embodiment of the invention. In order to adjust the horizontal position of the entire device 100 when the device 100 is hanged on the hanging element, the screw 34 is slightly loosened, the hanger 22 is rotated about the screw until the device is leveled with respect to the ground and the nut is fastened tightly back to fixate the position of the hanger.

To facilitate an accurate leveling, the device 100 is equipped with a level 36, such as a common bubble level, which is attached to the sidewall 16 of the housing 12. A level 36, is embedded on the bottom portion 16.2 of the sidewall of the housing. The level 36 provides an indication regarding the level orientation of the monitoring device 100, and in particular, that of the solar radiation sensor 110. The cavity 20 of the housing 12, is large enough to leave space below and above the hanger 22 to allow some degree of rotating the hanger 22.

In order to assure that the hanging element 150 is below the solar radiation sensor when the monitoring device 100 is hung, the upper wall 26 of the hanger is located bellow the exposed surface of the solar radiation sensor.

Note that the hanger 22 in FIG. 1A is slightly tilted with respect to an x-y plane about the screw 34, as it would for leveling the monitoring device 100 when it is hung on a tilted wire.

A hygrometer-thermometer (not shown) is placed inside the housing 12 adjacent to an aperture covered with a perforated cover 38 which is secured with a sensor cup 40 to the housing with the aid of two screws 42.

A protruding aperture 44 in the bottom 14 end of the housing 12 allows the exit of a connection to ground sensor(s) and/or a wind detector (not shown).

In the present exemplary embodiment, with reference to FIG. 1C, a joint 45 connects a top section 16.1 of the housing with bottom section 16.2 of the housing. The joint can be threaded or comprising a groove and a fixation pin or any other method known in the art for reversibly joining two parts. The division of the housing into separate sections enables opening of the housing, for example to replace batteries or a replace a sensor. The joint of the two sections of the housing may be sealed with an O-ring.

In the present example a L-shaped groove 19 in the top portion of the housing starting from the rim 18.1 functions as a fixation mechanism to a lateral pin extending from the inner wall of the cover 60 of the solar radiation sensor 110 defining a locking mechanism for the cover 60 and the housing 12.

An on/off rubber sealed and covered button 46 protrudes from the sidewall 16.1 through an aperture (not shown) in the sidewall 16.1. The sidewall 16.1 also comprises a perforated aeration aperture 47 for release of heat at the top section of the housing 12.

The shading sleeve 48 comprises a sidewall 52 having a bottom end 50 which in this embodiment is open, and allows sliding of the shading sleeve 48 over the housing top down (with respect to the housing) until the inner wall of the top end 58 of the shading sleeve 48 joints the cover of the solar radiation cover 60. Making reference to FIG. 2B, the two opposite slots 62 are open ended at the bottom 64 and closed ended at the top 66 allowing the sliding of the hanging element 150 through the slots 62 of the shading sleeve 48. In some embodiments the shading sleeve 48 rests on the hanging element 150, while the top ends 66 of the slots 62 serve as a contact points with the hanging element 150, which assist in locking the device to its position on the hanging element.

The shading sleeve 48 further comprises shades 54 and slits 56. In some embodiments the shading sleeve lacks shades and slits, and in some embodiments other forms of apertures in the shading sleeve provide both air-exchange and shade to the housing (e.g. multiple diagonal channels). A solar radiation sensor cap 60 covers the solar radiation sensor 110. The solar radiation sensor cap 60 provides protection to the solar radiation sensor 110 and attenuates the intensity of the radiation reaching the solar radiation sensor 110. The attenuation is normalized when calculating the real solar radiation influx.

A peripheral collar (not shown) extending from an inner circumference proximal to the top of inner wall of the shading sleeve 48 inwards and upwards to the top end 58 is compatible with a collar 70 of the solar radiation sensor cover 60 allowing the sleeve to reversibly snatch onto cover 60. Ventilation slits 68 are located proximal to the upper end of the sidewall of the shading sleeve 48.

FIGS. 2A through 2C depict the monitoring device in its assembled form, i.e. when the shading sleeve is assembled to the housing, while the monitoring device is hanging on a hanging element (e.g. a wire). As can be clearly seen, the shading sleeve 48 covers and shades the top portion of the housing 16.1. In this example, the shading sleeve 48 covers and shades the portion of the housing accommodating the hygrometer-thermometer. The longitudinal slots 62 are aligned with the side openings of the hanger 22 which allows the hanging element 150 to pass through the hanger 22 and through the shading sleeve 48, thus allowing the assembly of the sleeve 48 on the housing 12 while the housing 12 is hanging on the hanging element 150. The solar radiation sensor 150 is fully exposed to receive any source of light above the sensor 110.

Figure 3A:
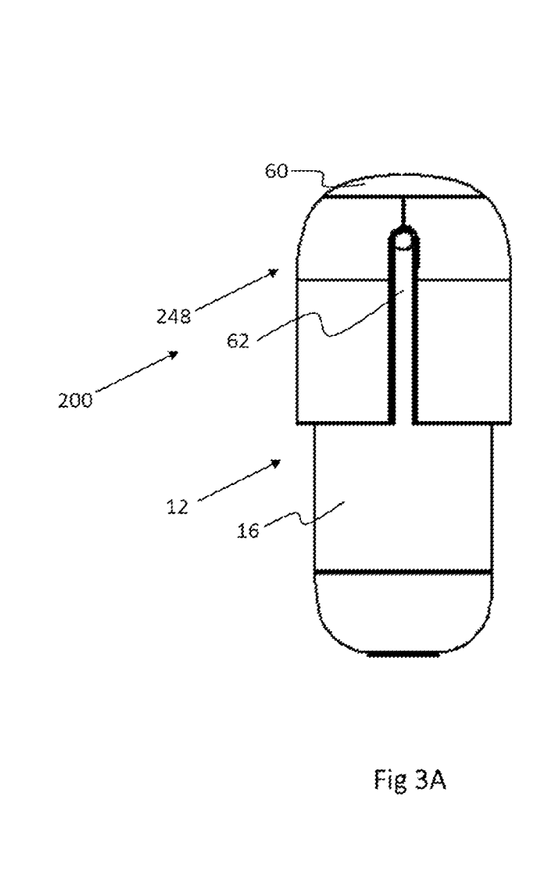
FIG. 3A depicts a side view schematic representation of a monitoring device in an assembled form (hanging on a wire) according to an embodiment of the invention in accordance with FIG. 4.
Figure 3B:
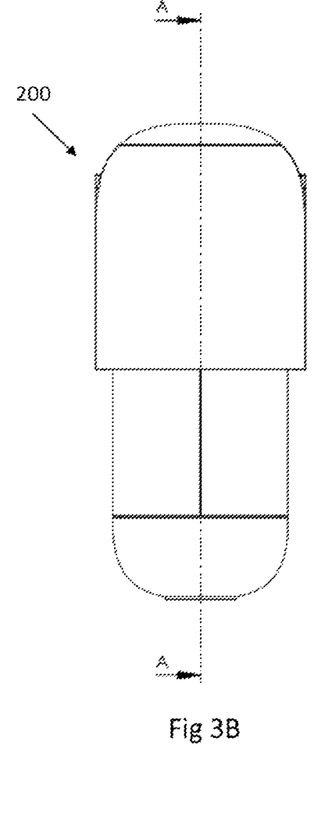
FIG. 3B depicts a front view schematic representation of a monitoring device in an assembled form (hanging on a wire) according to an embodiment of the invention in accordance with FIG. 3A.
Figure 3C:
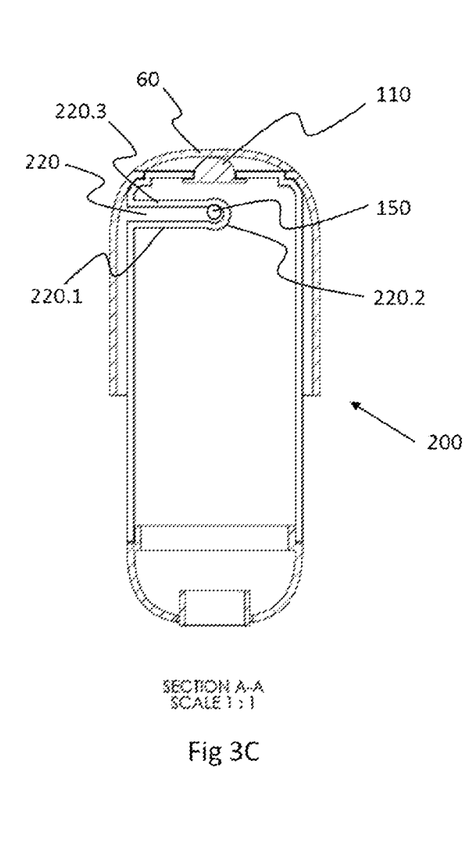
FIG. 3C depicts a cross sectional schematic representation of an assembled monitoring device according to an embodiment of the invention in accordance with FIG. 3B.

Reference is now made to FIGS. 3A to 3C depicting another monitoring device 200 according to an embodiments of the invention. The shading sleeve 248 in this embodiment lacks the shadings and the slits which are present in the embodiment represented by device 100. In addition, the cavity 220 functions as the hanger and is defined by bottom wall 220.1, inner sidewall 220.2 and top wall 220.3. The cavity 220 is designed to accommodate the hanging element 150 securely by holding it with the compatible structure of the inner wall 220.2. Instead of leveling the housing as done in the case of monitoring device 100, here the solar radiation sensor itself is leveled by its own leveling means such as a leveling motor which is placed on a stage and connected to the solar radiation sensor (not shown) or manually by mechanical means.

Figure 4:
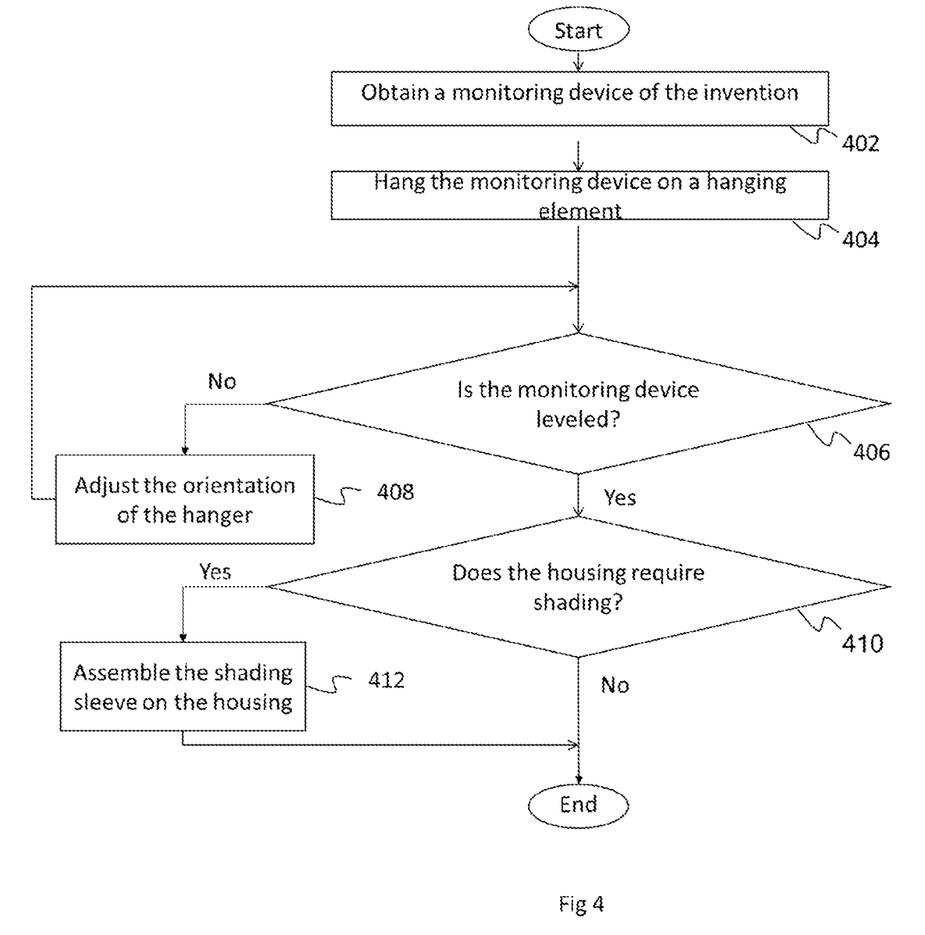
FIG. 4. depicts a flow chart diagram of a method for installing a monitoring device in an agricultural facility according to an embodiment of the invention.

Reference is now made to FIG. 4 depicting a flow chart diagram demonstrating a method of installation of a monitoring device in accordance with an embodiment of the invention.

The user (in most cases—the farmer, but a dedicated installer may replace the farmer) obtains a monitoring device of the invention (402) and hangs the monitoring device in a selected location in a field, indoor agricultural facility, orchard or garden (404). The person of skill in the art would know how to choose a preferable site in the vicinity of the crop for installing the monitoring device in order to receive optimal data for calculating environmental conditions of the crop.

The Penman equation dictates to measure parameters 2 meters above the ground. However for practical reasons this is not always feasible as explained earlier. Any deviation from placing the radiation sensor at 2 meters above the ground is normalized in the calculation which is later conducted elsewhere.

The hanging is performed by inserting the hanging element, may it be a cable, a wire, a string or a hose, through the cavity of the hanger which is located inside the cavity of the housing, all the way into the inner cavity of the hanger where the hanging element is securely placed. In embodiments where the cavity of the housing functions as the hanger—the above step is performed on the cavity of the housing accordingly.

The user examines whether the device is leveled (406). When the monitoring device comprises a level, in particular a bubble level, then the farmer can be assisted with the level to determine if the device is leveled or not.

If the device is not leveled, the user adjusts the orientation of the hanger (408) according to the type of hanger and leveling component at hand and may be assisted with the level, to determine that the device has reached a leveled position.

For example, if the hanger is a tubular rail attached to the housing with a screw—releasing the screw, adjusting the position of the hanger inside the cavity, and fastening the screw to fixate the hanger in the new position.

If the hanger is a set of a pair of hooks which are adjustably fixated into the bottom wall of the cavity— changing the height of the appropriate hook, i.e. if the device tilts to the right—elevate the left hook by pulling it upwards.

If the leveling means is a stage on which the solar radiation sensor is placed—adjusting the position of the stage accordingly by tilting it with respect to an x-y plane and affixing it in a leveled orientation.

If the device or the solar radiation sensor remain unleveled, the leveling step (408) is reiterated until obtaining a leveled device hanging on the hanging element.

Finally, if the housing comprises a sensor which requires shading such as a thermometer or hygrometer (410)— assembling the shading sleeve with the housing (412) while aligning the opening of the slot(s) of the shading sleeve with the hanging element and sliding the hanging element through the slot(s) of the shading sleeve until the shading cover is attached to the housing.

The invention claimed is:

1. A monitoring device, comprising:
    a housing adapted to accommodate at least a solar radiation sensor, the housing comprising a bottom end, a top end, and a peripheral sidewall extending from the bottom end to the top end, wherein the top end of the housing comprises a top end aperture adapted to allow a solar radiation sensor to be exposed through the top end aperture;
    a solar radiation sensor positioned in a top portion of the housing such that the solar radiation sensor is exposed through the top end aperture; and
    a hanger comprising a top end and being attached to the peripheral sidewall of the housing, the top end of the hanger located at the same level as or below the top end of the housing and adapted to hang the housing on a hanging element.

2. The monitoring device according to claim 1, further comprising a leveling component for leveling the solar radiation sensor.

3. The monitoring device according to claim 1 wherein the solar radiation sensor is characterized by at least one of: (i) having full exposure to any light source above the solar radiation sensor; or (ii) positioned at the same level or above hanging element when the monitoring device is hanged on the hanging element.

4. The monitoring device according to claim 1, further comprising an operational circuit comprising a communication component for receiving data from the solar radiation sensor and optionally from at least one other optional sensor for transmitting said data to a remote system, the operational circuit is optionally in communication with a system providing recommendations for a grower based on the data received from the monitoring device.

5. The monitoring device according to claim 4 wherein the data is collected for providing evapotranspiration parameters for in the vicinity of a plant or multiple plants to a system comprising installed instructions for calculating Penman-Monteith equation using said parameters and accordingly providing recommendations to a user.

6. The monitoring device according to claim 1 wherein the leveling component includes at least one member selected from the group consisting of:
    an adjustable fastener attaching the hanger to the housing;
    an adjustable fastener attaching the solar radiation sensor to the housing;

an adjustable fastener attaching a stage carrying the solar radiation sensor to the housing; and a mechanical motor connected to the solar radiation sensor or a stage carrying the solar radiation sensor capable of leveling the solar radiation sensor.

7. The monitoring device according to claim 1 wherein the peripheral sidewall of the housing defines an open sided cavity extending inwards towards the center of the housing, the cavity accommodating the hanger.

8. The monitoring device according to claim 1 wherein the hanger is attached to the peripheral sidewall and the weight of the hanger is adapted to dictate a center of mass of the monitoring device at the contact point between the hanging element and the hanger when the device is hanging on the hanging element.

9. The monitoring device according to claim 1 wherein the hanging element includes at least one member selected from the group consisting of a wire, a cable, a string, a nail, a pipe, a branch of a plant, and a hose.

10. The monitoring device according to claim 1 wherein the hanger is selected from the group consisting of:

a linear tubular rail horizontally attached to the peripheral sidewall of the housing comprising two opposing open side ends, a horizontal opening from one side end to the other side end, and a side opening at each of the two ends of the tube, wherein the horizontal and side openings being complementary to accommodate a hanging element;

a set of at least two hooks having an opening of at least the diameter of a fishing line;

at least one screw connected to at least two strings, and a snap lock conduit.

11. The monitoring device according to claim 1, further comprising a level.

12. The monitoring device according to claim 1, wherein the housing is adapted to accommodate at least one more sensor for detecting agricultural parameters.

13. The monitoring device according to claim 12 wherein the at least one more sensor is at least one of a thermometer or a hygrometer; and wherein the monitoring device further comprising:

a shading sleeve comprising a peripheral sidewall optionally comprising spaced shades, the peripheral sidewall adapted to shade the portion of the housing accommodating the at least one of the thermometer or the hygrometer, and allow air exchange between the housing and the ambient air surrounding the monitoring device, a top end opening, a bottom end and at least one slot compatible with the dimensions of the hanging element allowing the hanging element to pass through said at least one slot; and the housing further comprising an aperture fit to expose at least one of the thermometer or the hygrometer to the air surrounding the housing.

14. The monitoring device according to claim 13 wherein the shading sleeve comprises an open bottom end, and two longitudinal slots, the slots having an opening on the bottom end such that a wire on which the hanger is hanged can be inserted through the two slots; the shading sleeve optionally comprises two parts which are reversibly attached to each other having a horizontal slot positioned parallel to the position of the hanging element when the sleeve is assembled on the housing when the housing is hanging on the hanging element.

15. The monitoring device according to claim 1, further comprising a solar radiation sensor, a thermometer, and a hygrometer.

16. The monitoring device according to claim 1 wherein the bottom end of the housing includes an aperture adapted for a passage of a cable connection between the communication circuit and at least one of a wind sensor or a soil sensor for determining soil parameters, the soil sensor is optionally selected from at least one of a tensiometer, pH meter, nutrients sensor, or a soil moisture sensor.

17. The monitoring device according to claim 1 wherein the monitoring device is adapted to collect and transmit agricultural parameters in an indoor plant growing location, field, orchard, or garden, wherein the indoor plant growing location is optionally selected from a greenhouse, a cold frame, a growing room and a growing warehouse.

18. The monitoring device according to claim 1 wherein the hanger is attached to the peripheral sidewall of the housing with a fastener.

19. A method for installing a monitoring device in an indoor agricultural facility, orchard, or field, the method comprising:

a. obtaining the monitoring device as defined in claim 1;

b. hanging the monitoring device above a crop on a hanging element optionally selected from the group consisting of a wire, pipe and a hose;

c. leveling the solar radiation sensor optionally by loosening a fastener attaching the hanger to the housing, then adjusting the orientation of the hanger until the monitoring device is level and fastening the adjustable fastener to fixate the orientation of the hanger; and d. if the monitoring device further comprising at least one of a thermometer or a hygrometer then covering the housing with the shading sleeve as defined in claim 13 while inserting the hanging element through the slots of the shading sleeve;

to obtain a monitoring device hanged on a hanging element comprising a leveled solar radiation sensor fully exposed to any source of light above the solar radiation sensor.

20. The method according to claim 19, further comprising hanging the monitoring device above the crop and the data is used for calculating Penman equation or the Penman-Monteith equation.

21. A kit comprising the monitoring device as defined in claim 1 and instructions for installing the monitoring device comprising the method as defined in claim 19.

22. The kit according to claim 21, further comprising programmable instructions being installed on a processing unit of the device for managing data collected sensors of the device.

* * * * *